United States Patent
Tanaka

(10) Patent No.: US 6,726,568 B2
(45) Date of Patent: Apr. 27, 2004

(54) COIL SHAFT AND METHOD FOR FABRICATING SAME

(75) Inventor: Toshizumi Tanaka, Saitama-ken (JP)

(73) Assignee: Fuji Photo Optical Co., Ltd., Omiya (JP)

(*) Notice: Subject to any disclaimer, the term of this patent is extended or adjusted under 35 U.S.C. 154(b) by 0 days.

(21) Appl. No.: 09/808,169

(22) Filed: Mar. 15, 2001

(65) Prior Publication Data

US 2001/0052721 A1 Dec. 20, 2001

(30) Foreign Application Priority Data

Mar. 31, 2000 (JP) ........................................ 2000-098790

(51) Int. Cl.⁷ ................................................. F16C 1/06
(52) U.S. Cl. ............................ 464/52; 464/58; 74/502.5
(58) Field of Search ............................... 464/52, 53, 57, 464/58, 59, 60; 600/459; 267/168, 180, 181; 74/500.5, 502.4, 502.5; 297/367

(56) References Cited

U.S. PATENT DOCUMENTS

| | | | | |
|---|---|---|---|---|
| 274,715 A | * | 3/1883 | Buckley | ...................... 267/180 |
| 1,995,421 A | * | 3/1935 | Goldberg | ...................... 464/53 |
| 2,401,100 A | * | 5/1946 | Pile | ........................... 464/58 X |
| 2,438,380 A | * | 3/1948 | Arens | ......................... 74/502.5 |
| 3,135,131 A | * | 6/1964 | Marr | .......................... 74/502.5 |
| 4,395,924 A | * | 8/1983 | Callahan | .............. 74/424.77 X |
| 4,889,327 A | * | 12/1989 | Seyler | ........................ 267/168 |
| 6,264,183 B1 | * | 7/2001 | Meier et al. | ............ 267/168 X |

FOREIGN PATENT DOCUMENTS

| | | | | |
|---|---|---|---|---|
| GB | 1028327 | * | 5/1966 | .................. 464/58 |
| JP | 1-214349 | | 8/1989 | |

\* cited by examiner

*Primary Examiner*—Greg Binda
(74) *Attorney, Agent, or Firm*—Oblon, Spivak, McClelland, Maier & Neustadt, P.C.

(57) ABSTRACT

A coil shaft or tube to be fitted into a flexible sleeve to serve as a flexible rotation transmission shaft, containing a partially coarsely wound coil shaft formed by winding around a core a plural number of unit wires which are arranged in intimately parallel relation with each other in the fashion of a single flat metal strip, and extracting a dummy wire afterwards from a resulting tightly wound coil shaft to form coarsely wound portions where helices of certain adjacent unit wires spaced apart in the axial direction and in certain portions of the coil shaft.

3 Claims, 3 Drawing Sheets

COIL SHAFT AND METHOD FOR FABRICATING SAME

BACKGROUND OF THE INVENTION

1. Field of the Art

This invention relates to a coil shaft which is particularly suitable for use as a flexible rotation transmission member of a control cable or the like, and a method for fabricating such coil shafts.

2. Prior Art

Control cables, with a rotary member at a distal end, generally have a flexible rotation transmission shaft fitted in a flexible sleeve. As a proximal end of the flexible transmission shaft is turned about its axis, the rotation is transmitted to the other fore distal end of the flexible shaft to which a rotary member is connected. The proximal end of the flexible shaft is connected to a rotational drive mechanism. The flexible sleeve is rotatable relative to the flexible transmission shaft, and fixedly connected to a non-rotatable member at least at its one end, preferably at its opposite ends. The rotational drive mechanism is provided with rotational drive means like an electric motor thereby to turn the proximal end of the flexible transmission shaft about its axis. The rotation of the proximal end of the flexible transmission shaft is followed by the rotary member which is connected to the fore distal end of the flexible transmission shaft. If necessary, the flexible transmission shaft can be rotated manually.

In the case of a rotation transmitting control cable of this sort, rotation has to be transmitted quickly and securely from one to the other end of a flexible transmission shaft which is fitted in a flexible sleeve. Besides, the flexible transmission shaft should be flexibly bendable in arbitrary directions, and should be able to transmit rotations even in a bent form securely with less resistance to rotation and smoothly under a smaller load.

Considering the general requirements as mentioned above, it has been the usual practice to employ, as a flexible transmission shaft of a control cable, a coil shaft which is formed by helically winding spring type metal wires. In order to transmit rotation more securely and accurately, the flexible transmission shaft is at least constituted by a coil shaft of a double coil construction having inner and outer coils. It has also been known in the art to employ a flexible transmission shaft of a triple coil construction especially for the purpose of transmitting rotations in both forward and reverse directions. Further, in order to prevent delays in transmitting rotation to a rotary member and to stabilize operation of the rotary member, the metal wires of the coil shaft are wound tightly in such a way that the interstices between the individual helices are completely closed. Further, each coil of the coil shaft can be constituted by either a single wire winding or a multiple-wire winding having a plural number of wires arranged flatly side by side in the fashion of a strip.

No matter whether a coil shaft is of a single wire winding type or a multiple-wire winding type, tightly wound coils are flexible in bending directions and capable of transmitting rotations quickly and securely to a fore distal end of the coil shaft. Namely, in a tightly wound state, a coil is no longer contractible in length, so that, upon applying a rotational force to a proximal end of the coil in a tightening direction, it is tightened into a substantially rigid from its proximal to fore distal end without undergoing changes in diameter. Therefore, the rotational force can be transmitted securely to the distal end to which a rotary member is connected. The coil shaft is flexibly bendable, so that, when bent, interstices are opened up between helices on the outer side of a bent portion. However, this does not affect the rotation transmitting capability of the coil shaft because helices on the inner side of a bent portion are tightly pressed to each other all the more.

This sort of flexible transmission shaft of a control cable, which can be constituted by a single coil shaft or double or triple coaxial coil shafts, is normally fitted in a flexible sleeve as mentioned above. The gap width between the flexible transmission shaft and the flexible sleeve is held to a minimum since radial vibrations will occur to the flexible transmission shaft during rotation if there is a conspicuous difference between the outside diameter of the flexible shaft and the inside diameter of the flexible sleeve. When a control cable is flexed into a bent state, the flexible sleeve and the flexible transmission shaft within the flexible is flexed into a similar shape separately from each other. When in a bent state, the flexible sleeve is stretched on the outer side of a bent portion and contracted on the inner side of the bent portion, which is somewhat flattened in cross-sectional shape. In contrast, the tightly wound coils of the flexible transmission shaft undergoes substantially no changes neither in diameter nor in pitch of helices on the inner side of the bent portion, although the pitch of helices on the outer side of the bent portion is broadened to some extent. Namely, as a control cable is flexed into a bent form, the flexible sleeve is freely deformable but the flexible transmission shaft is considerably restricted in deformability. Especially, when a coil shaft is bent, a reaction force occurs in the coil shaft in a linear direction to resist a bending force. This resistance to a bending force becomes extremely large particularly in the case of a flexible transmission shaft which is constituted by multiple coil shafts.

For the reasons as stated above, when the control cable is bent, the flexible transmission shaft within the cable is partially pressed against an inner surface of the flexible sleeve. Accordingly, when the control cable is in a bent state and the flexible transmission shaft is pressed against an inner surface of the flexible sleeve, rotation of the flexible transmission shaft is met by a large resistance due to sliding contact of the flexible transmission shaft and sleeve. As a consequence, it becomes difficult for the flexible transmission shaft to transmit rotations smoothly, suffering from troubles such as increased load, irregular rotations and vibrations.

In addition, the internal cavity of a tightly wound coil shaft is substantially in a closed state, so that it is often found difficult to supply a liquid into the coil shaft which is fitted in a flexible sleeve. For instance, when there is a necessity for sealing a fluid in a hermetically closed coil shaft, this cannot be accomplished easily especially in the case of a multiple coil shaft which requires to replace air residues between inner and outer coils completely by a filling fluid.

SUMMARY OF THE INVENTION

With the foregoing situations in view, it is an object of the present invention to provide a coil shaft which is simple in construction and easy to manufacture, and which is improved in flexibility in bending directions.

It is another object of the present invention to provide a coil shaft which can transmit rotations smoothly under a light load when applied as a flexible rotation transmission shaft, despite freedom in bending flexibility.

It is still another object of the present invention to provide a coil shaft which permits to fill thereinto a fluid like a liquid from outside.

According to the present invention, in order to achieve the above-stated objectives, there is provided a multi-wire coil shaft having a plural number of metal wires helically wound together in intimately parallel relation with each other, the multi-wire coil shaft comprises coarsely wound portions where having helices of said wires are relatively spaced apart and being provided in or between tightly wound portions to take the shape of a partially coarsely wound coil shaft.

According to the present invention, there is also provided a method for fabricating a partially coarsely wound coil shaft as mentioned above, which essentially comprises the steps of: arranging a plural number of unit metal wires and at least one dummy wire intimately side by side and in parallel relation with each other like to present a shape of a single flat metal strip; helically winding the strip of wires around a round core to form a tightly wound coil shaft with helices of adjacent wires are tightly closed to each other; and removing the dummy wire from the multi-wire coil shaft to obtain a partially coarsely wound coil shaft.

The above and other objects, features and advantages of the present invention will become apparent from the following particular description of the invention, taken in conjunction with the accompanying drawings which show by way of example preferred embodiments of the invention. Needless to say, the present invention should not be construed as being limited to the particular forms shown.

DESCRIPTION OF PREFERRED EMBODIMENTS

Figure 1:
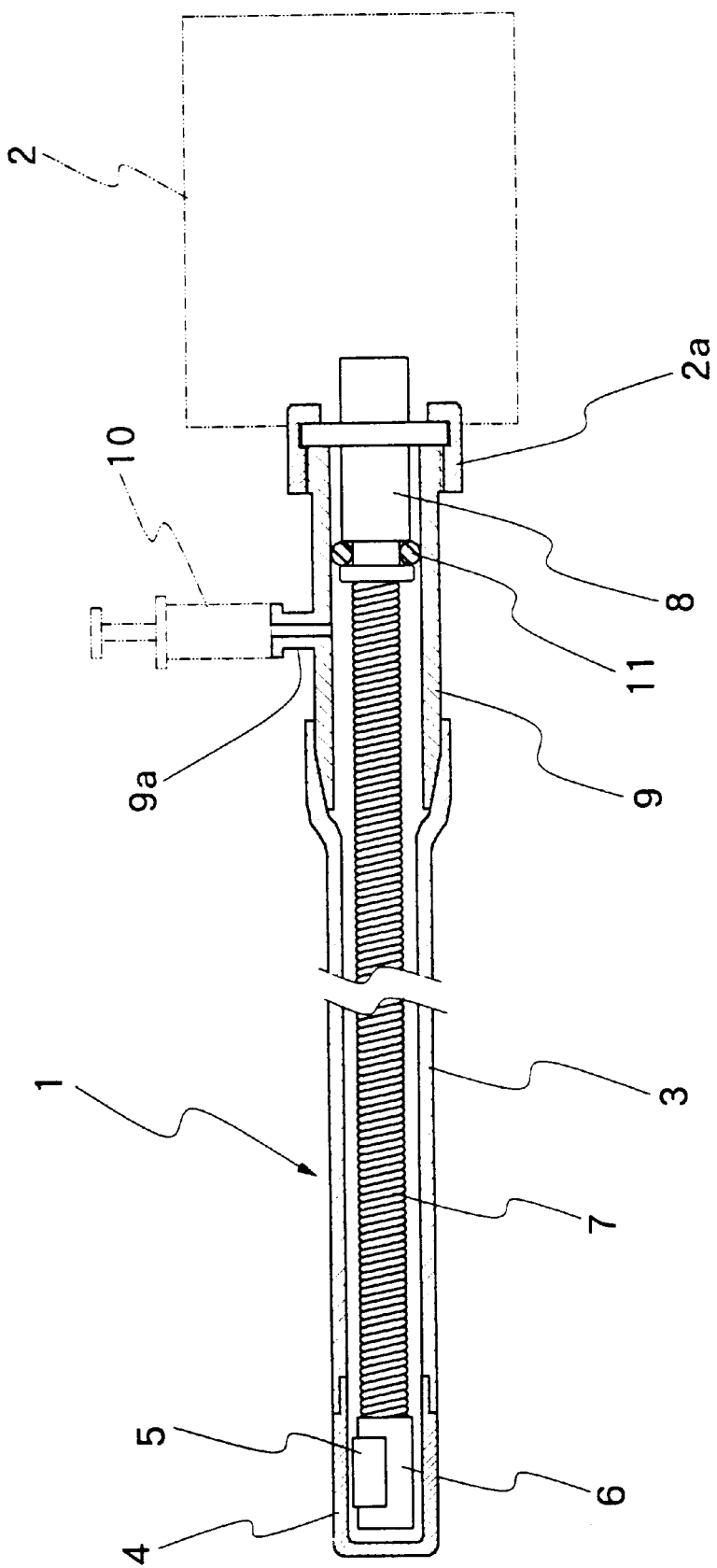
FIG. 1 shows in a schematic longitudinal section an ultrasound probe as an example of application of a coil shaft according to the present invention.

Hereafter, the present invention is described more particularly by way of its preferred embodiments. For example, the coil shaft according to the present invention can be employed by a control cable as a flexible rotation transmission shaft to transmit rotation by remote control to a rotary member which is attached to a fore distal end of the control cable. A control cable of this sort is fitted, for example, in an ultrasound probe as shown in FIG. 1, thereby to rotationally drive an ultrasound transducer element which is attached to a fore distal end of the probe and which is to be rotated by remote control at the time of radial scans. However, it is to be understood that an ultrasound probe is an example of application and the coil shaft according to the invention is not limited to this particular form of application.

In FIG. 1, indicated at 1 is an ultrasound probe itself, and at 2 is a rotational operating section. The ultrasound probe 1 has an ultrasound transducer element 5 rotatably mounted within a cap 4 of a rigid material which is connected to a fore distal end of an elongated flexible sleeve 3. The ultrasound transducer element 5 is of a radial scan type and rotatably mounted on a cradle-like support member 6 within the cap 4. In the case of the ultrasound probe 1, the ultrasound transducer element 5 on the support member 6 is a rotary member to be rotated by remote control, and the support member 6 is connected to a fore distal end of a flexible transmission shaft 7.

A control cable is largely constituted by the flexible sleeve 3 and the flexible transmission shaft 7 which is fitted in the flexible sleeve 3. Through this control cable, the ultrasound transducer element which has been introduced into a body cavity, for example, is rotationally driven by remote control to make radial scans. Accordingly, as rotational force is applied to a proximal end of the flexible transmission shaft 7, the latter is rotated about its axis within the flexible sleeve 3 to transmit the rotation to the support member 6 which is connected to the fore distal end of the flexible shaft. As a consequence, the ultrasound transducer element 5 on the support member 6 is rotated along with the latter. At the time of a radial scan, the ultrasound transducer 5 is put in rotation and driven to transmit an ultrasound pulse into a patient's body at predetermined angular intervals, while receiving echo signals of transmitted ultrasound pulses.

The proximal end of the flexible transmission shaft 7 is coupled with a rotational shaft 8 which is in turn coupled with an output shaft of a motor provided within the above-mentioned rotational operating section 2. On the other hand, the proximal end of the flexible sleeve 3 is fixedly connected to a fore end of a connector tube 9. The other proximal end of the connector tube 9 is detachable connected to an annular socket portion 2a provided on a housing of the rotational operating section 2. In the drawings, indicated at 10 is a fluid feed means which is provided particularly for the purpose of feeding an ultrasound transmission medium into internal spaces of the flexible sleeve 3. This fluid feed means is detachably connected to a fluid feed port 9a which is provided on the connector tube 9. Through this fluid feed means 10, an ultrasound transmission medium is supplied into the entire internal spaces of the ultrasound probe from the flexible sleeve 3 to the end cap 4. A resilient seal member 11 is interposed between the rotational shaft 8 and the inner periphery of the connector tube 9, thereby retaining the inside of the ultrasound probe 1 in a hermetically sealed state to prevent leakage of the filled-in ultrasound transmission medium. Although omitted in the drawings, a signal cable to the ultrasound transducer element 5 is passed through the internal space of the flexible transmission shaft 7. The proximal end of the signal cable is connected to a slip ring and a rotary connector within the rotational operating section 2.

Figure 2:
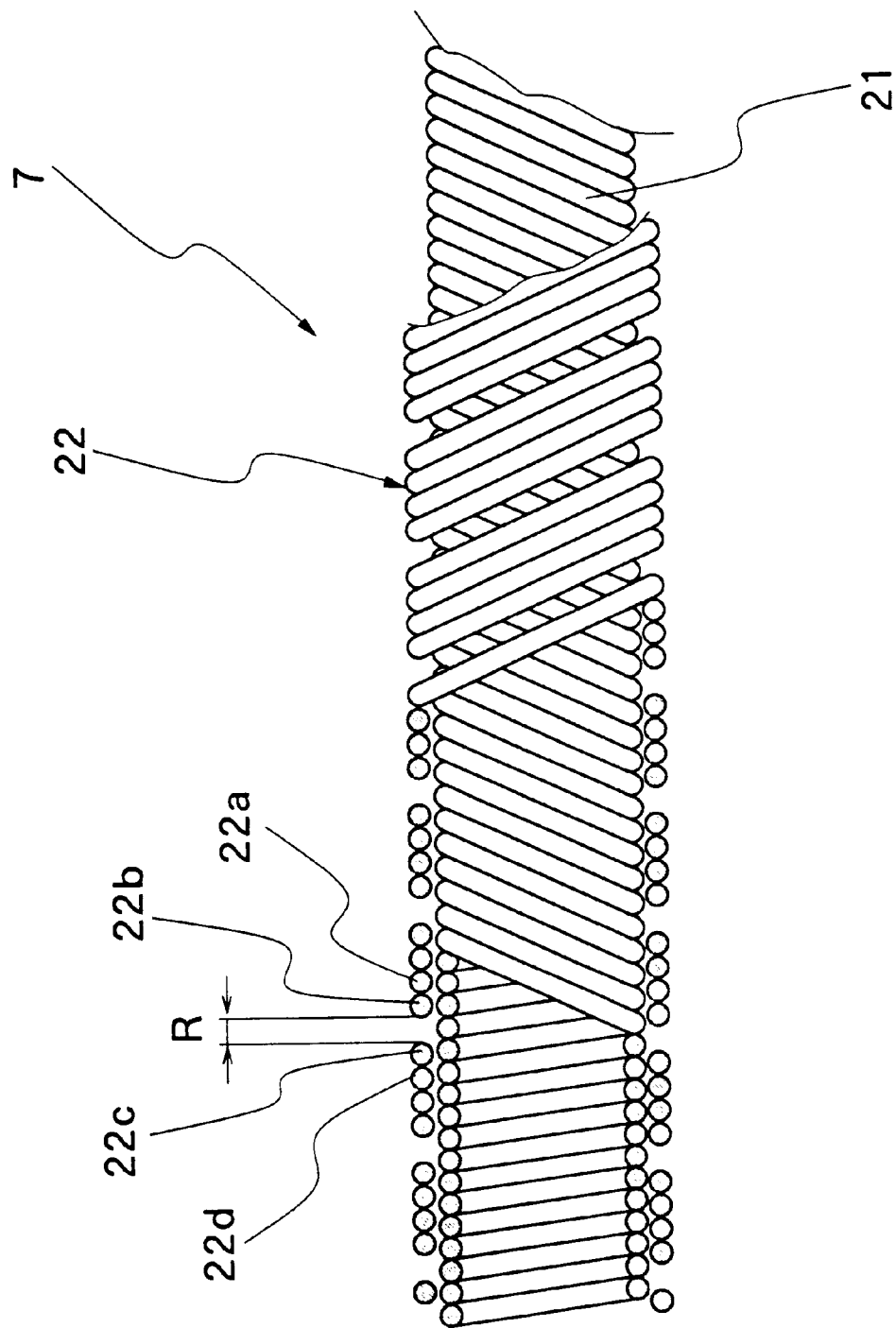
FIG. 2 is a partly sectioned schematic view of a coil shaft according to the present invention, showing the construction of the coil shaft in greater detail.

Now, referring to FIG. 2, the flexible transmission shaft 7 is shown in a partly sectioned view. This flexible transmission shaft 7 has a double coil shaft construction. As seen in that figure, the flexible transmission shaft 7 is of a double coil shaft type having an inner coil shaft 21 and an outer coil shaft 22. The inner coil shaft 21 consists of a tightly wound coil shaft, while the outer coil shaft 22 consists of a partially coarsely wound coil shaft.

In this instance, the outer coil shaft 22, which is a partially coarsely wound coil, is a coil consisting of four metal wires which are helically wound together in the fashion of a single flat metal strip, and is constituted by four unit coils 22a to 22d. These four unit coils 22a to 22d are wound tightly to each other without being intervened by a gap therebetween except the unit coils 22b and 22c which are separated from each other by a gap space R of a predetermined width. Namely, the outer coil shaft 22 is tightly closed between the unit coils 22a and 22b, between unit coils 22c and 22d and unit coils 22d and 22a and coarsely opened between unit coils 22b and 22c.

On the other hand, the inner coil shaft 21 is a tightly wound coil having respective helices closed tightly to each other over its entire axial length. This inner coil shaft 21 can be formed by tightly winding a single flat metal strip. However, for the purpose of bringing the inner and outer coil shafts into conformity with each other in bias angle and at the same time for smooth transmission of rotation, the inner coil shaft 21 may be constituted by a multiple unit coils similarly to the outer coil shaft 22. The inner coil shaft 21 is formed to have an outside diameter which is substantially same as the inside diameter of the outer coil shaft 22, so that the two coil shafts 21 and 22 are brought into intimate contact with each other when the inner coil shaft 21 is fitted into the outer coil shaft 22 to form the flexible transmission shaft 7.

As described above, the partially coarsely wound outer coil shaft 22 of the flexible transmission shaft 7 has the helices of the unit coils 22b and 22c coarsely separated from each other by a gap space R. When the outer coil shaft 22 is flexed into a bent form, the helices of the unit coils 22b and 22c are closed toward each other on the inner side of a bend portion permitting to bend the coil shaft 22 quite easily with less resistance. Accordingly, the flexible transmission shaft 7 becomes to have higher flexibility in bending directions. This means that, when the ultrasound probe 1 is introduced into a body cavity, it can be bent easily along a path of insertion with less resistance due to rectilinear reaction forces. It follows that the ultrasound probe 1 can be inserted into a body cavity smoothly with less pains on the part of a patient.

Despite the provision of coarsely wound portions, the outer coil shaft 22 which is constituted by a multiple number of unit coils 22a to 22d substantially tightly wound in other major portions, namely, between the unit coils 22a and 22d, between the unit coils 22a and 22b, between the unit coils 22c and 22d and between the unit coils 22d and 22a. Therefore, during a rotation transmitting operation, almost no changes occur to the width of gap spaces between the helices of the unit coils 22b and 22c no matter whether the flexible transmission shaft is in a rectilinear form or bent form. The provision of the coarsely wound portion will not affect the performance quality in rotation transmission, and rotations can be transmitted through the flexible transmission shaft 7 without delays in the same manner as flexible transmission shafts without coarsely wound portions.

When the flexible transmission shaft 7 is bent within the flexible sleeve 3, helices of the unit coils 22b and 22c on the inner side of a bent portion are moved toward each other to narrow down the gap spaces therebetween. This behavior of the coil helices serves to prevent a difference in length from occurring between the flexible sleeve 3 and the flexible transmission shaft 7 in the bent portion and to lessen reaction forces against a bending action. Accordingly, even if the flexible transmission shaft 7 is pressed against inner surfaces of the flexible sleeve 3, the pressing force becomes extremely small. As a consequence, during rotation, the friction which inevitably results from sliding contact between the flexible transmission shaft 7 and the inner surfaces of the flexible sleeve 3 can be diminished to a considerable degree. Besides, the coarsely wound portions in the outer coil shaft 22 contribute to reduce the contact areas of the flexible transmission shaft 7 with the inner surface of the flexible sleeve 3. Accordingly, while the flexible transmission shaft 7 is put in rotation in sliding contact with the flexible sleeve 3, the friction against the inner surface of the latter is reduced to a significant degree to permit the flexible transmission shaft 7 to transmit rotations smoothly under a reduced load and with less irregularities in rotational movements.

Further, the outer coil shaft 22 contains gap spaces between helices in the coarsely wound portions. These gap spaces are widened to a relatively large width when the flexible transmission shaft 7 is straightened into a rectilinear form. Accordingly, at the time of supplying a fluid ultrasound transmission medium into the flexible sleeve 3 from the fluid feed portion 10, the fluid can be easily impregnated into the flexible tube 3 in a favorable manner for replacement of air. Namely, air in the ultrasound probe 1 can be replaced by an ultrasound transmission medium quickly in a reliable manner.

Coarsely wound portions may be provided not only in the outer coil shaft 22 but also in the inner coil shaft 21 in order to impart the flexible transmission shaft with higher flexibility in bending direction, to minimize reaction forces tending to straighten the flexible transmission shaft against a bending force, for more smooth supply of an ultrasound transmission medium. Furthermore, in a case the flexible transmission shaft 7 is of a triple coil shaft type, it is possible to employ the partially coarsely wound coil shaft construction for all or at least one of its coil shaft members.

In this instance, the partially coarsely wound coil shaft 22 can be fabricated by a method as described below. In the following description, by way of example a partially coarsely wound coil shaft is shown as being formed of four coils. However, it is to be understood that the number of unit coils and the gap width between helices in coarsely wound portions can be determined arbitrarily, not to mention the number of coarsely wound portions in a coil shaft. For example, if desired, a coil shaft can be formed of six unit coils, which are arranged to contain two coarsely wound portions in two adjacent or distant positions.

Figure 3:
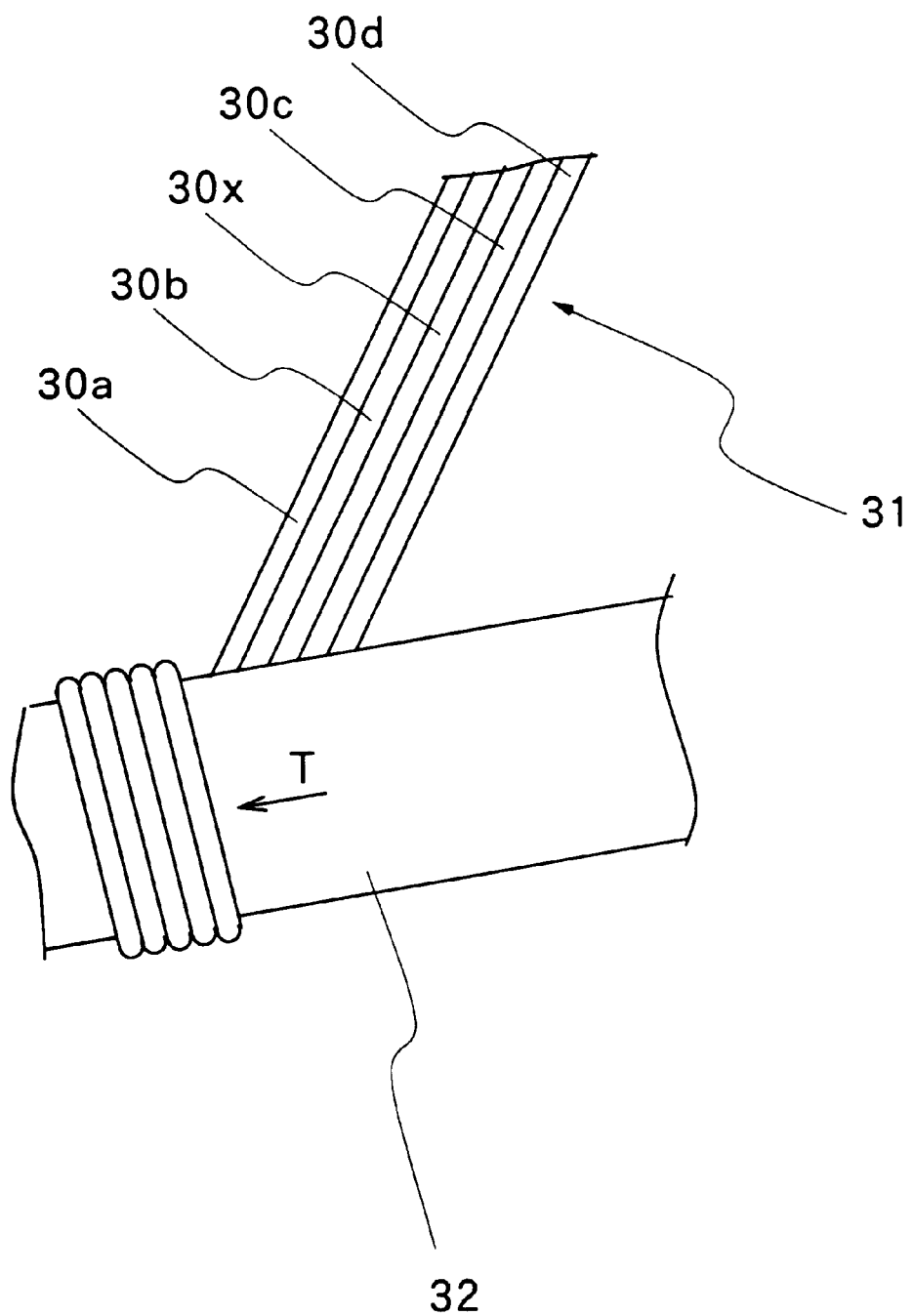
FIG. 3 is a schematic illustration explanatory of a coil winding state of a coil shaft manufacturing process.

As shown in FIG. 3, five wires of the same gage are used in fabricating a partially coarsely wound coil shaft consisting of four unit coils. Of these five wires, four wires 30a to 30d are metal wires to be wound unit coils 30a to 30d while the remaining one 30x is a dummy wire which will not contribute as a structural part of the coil shaft. In this instance, all of the five wires 30a to 30d and 30x are tightly wound together to form a multi-thread coil shaft but the dummy wire 30x is removed and separated afterwards from wires 30a to 30d, leaving coarsely wound coil portions between tightly wound coil portions formed by the wires 30a to 30d of the resulting coil shaft. Accordingly, for example, it suitable to use for the dummy wire a super-resilient spring steel wire which is immune from permanent deformation and can quickly restore an original rectilinear shape upon removing a deforming external force therefrom. Alternatively, it is possible to use a wire of shape memory alloy or resin which readily uncoil of itself or which can be easily uncoiled under certain temperature conditions. Further, it is also possible to use, for example, a wire of low melting point synthetic resin which melts down upon application of heat.

A dummy wire 30x is located in those positions which form coarsely wound portions in the resulting coil shaft to be fabricated. For example, a dummy wire 30x is interposed between second and third wires 30b and 30c, and all of the five wires 30a to 30d and 30x are arranged intimately side by side and in parallel relation with each other to present a shape a single elongated flat metal strip. After clamping in position one end by a suitable means, the assembled wire strip 31 is helically wound around a round core member 32 to form a tubular multi-wire coil shaft as shown in FIG. 3. In this winding stage, a force is applied to the assembled wire strip 31 as indicated by an arrow T so that the respective unit wires, including the dummy wires, are pressed tightly to each other and to preceding helices as they are wound around the core member 32. In this instance, the pressing force T should be large enough for deforming the unit wires 30a to 30d to such an extent as to remain in the tightly wound state even after the pressing force T is removed therefrom. By so doing, the coil shaft can be retained stably in shape even after separation from the core member 32.

After winding the assembled wire strip 31 into a multi-wire coil shaft, the fixed end of the wire strip 31 is cut off and separated from the core member 32. Upon separating the coil shaft into a free state, the dummy wire 30x which is formed of super-resilient spring steel tends to uncoil itself and restore a rectilinear shape. Therefore, the dummy wire 30x can be automatically extracted and separated from other unit wires of the coil shaft without necessitating an additional operation for this purpose. As a consequence, there is obtained a partially coarsely wound coil shaft in which coarsely wound portions are formed partially between tightly wound portions and uniformly along the entire length of the coil shaft. In this embodiment, removal of the dummy wire 30x will provide a gap space substantially corresponding to a cross section of a diameter of one unit coil when the coil shaft 22 is substantially unflexed (i.e., the gap space corresponding to the diameter of the dummy wire 30x that is that same as the diameter of the unit wires 30a–30d).

In this connection, the extraction of a dummy wire at the end of the coil shaft winding operation becomes extremely easy and the same dummy wire can be used repeatedly in a case it is formed of super-resilient spring steel as described above. Further, in a case of a dummy wire of a shape memory alloy or of a shape memory synthetic resin, it is possible to transform the wire into a rectilinear shape or into a larger diameter by changing temperature conditions, for example, by application of heat, for facilitating its extraction and separation after a coil shaft winding operation. Furthermore, in the case of a dummy wire of a low melting point plastic, it can be extracted or removed by immersing a resulting coil shaft as a whole in a solvent or by heating the coil shaft.

What is claimed is:

1. A control cable for use in transmitting rotations to a rotating member by remote control, comprising:

a flexible shaft having at least an inner coil shaft and an outer coil shaft; and a flexible sleeve encasing said flexible shaft;

wherein at least the outer coil shaft comprises a multi-wire coil shaft including a plural number of unit coils formed by helically winding together a corresponding number of metal wires of a predetermined diameter with at least one dummy wire of the predetermined diameter tightly to each other in a single flat metal strip, and one of said unit coils of said outer coil shaft having helices spaced apart from helices of at least one adjacent unit coil by a helical gap space opened up in the outer shaft by removal of said dummy wire to provide coarsely wound coil portions and tightly wound coil portions alternately along an entire axial length of said outer coil shaft.

2. A control cable as recited in claim 1, wherein said outer coil shaft with coarsely and tightly would coil portions is fitted coaxially around said inner coil shaft that is in the form of a totally tightly wound coil shaft.

3. A control cable for use in transmitting rotations to a rotating member by remote control, comprising:

a flexible shaft in the form of a double coil shaft having at least an inner coil shaft and an outer coil shaft; and a flexible sleeve encasing said flexible shaft;

wherein at least the outer coil shaft comprises a multi-wire coil shaft including a plural number of unit coils formed by helically winding together a corresponding number of metal wires of a predetermined diameter tightly to each other in a single flat metal strip, and one of said unit coils of said outer coil shaft having helices spaced apart from helices of at least one adjacent unit coil by a gap space substantially corresponding to a diameter of a cross section of one unit coil when the outer coil shaft is substantially unflexed to provide coarsely wound coil portions and tightly wound coil portions alternately along an entire axial length of said outer coil shaft.

* * * * *